United States Patent [19]

Witiak et al.

[11] Patent Number: 4,683,087
[45] Date of Patent: Jul. 28, 1987

[54] ANTI-CANCER AGENTS AND PROCESSES FOR THEIR PREPARATION

[75] Inventors: Donald T. Witiak, Mt. Vernon; Ronald M. Glaser, Powell, both of Ohio

[73] Assignee: The Ohio State University Research Foundation, Columbus, Ohio

[21] Appl. No.: 725,167

[22] Filed: Apr. 23, 1985

Related U.S. Application Data

[63] Continuation of Ser. No. 526,895, Aug. 26, 1983, abandoned.

[51] Int. Cl.$^4$ .................. C07C 50/08; C07C 50/06
[52] U.S. Cl. ............................................. 260/396 R
[58] Field of Search ................................... 260/396 R Primary Examiner—Glennon H. Hollrah
Assistant Examiner—Raymond Covington
Attorney, Agent, or Firm—Sidney W. Millard

[57] ABSTRACT

Compounds of the formula

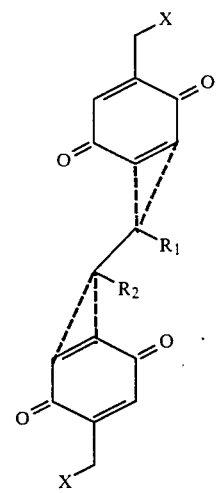

wherein $R_1$ and $R_2$ are either two hydrogen atoms or together form a methylene group, and each X is a bromo, iodo or tosyloxy group and the dotted bonds indicate that the central linkage is attached to the two phenyl rings at positions which are either meta to both $CH_2X$ groups or para to both such groups, possess anti-cancer activity.

The active compounds are prepared by multi-step syntheses beginning with dimethoxymethylbenzaldehydes or di(hydroxymethyl)methoxyphenols; many of the intermediates involved are themselves novel.

6 Claims, 6 Drawing Figures (I)

(II P)    (III P)    (IV P)

(II M)    (III M)    (IV M)

(I)

(II P)

(III P)

(IV P)

(II M)

(III M)

(IV M)

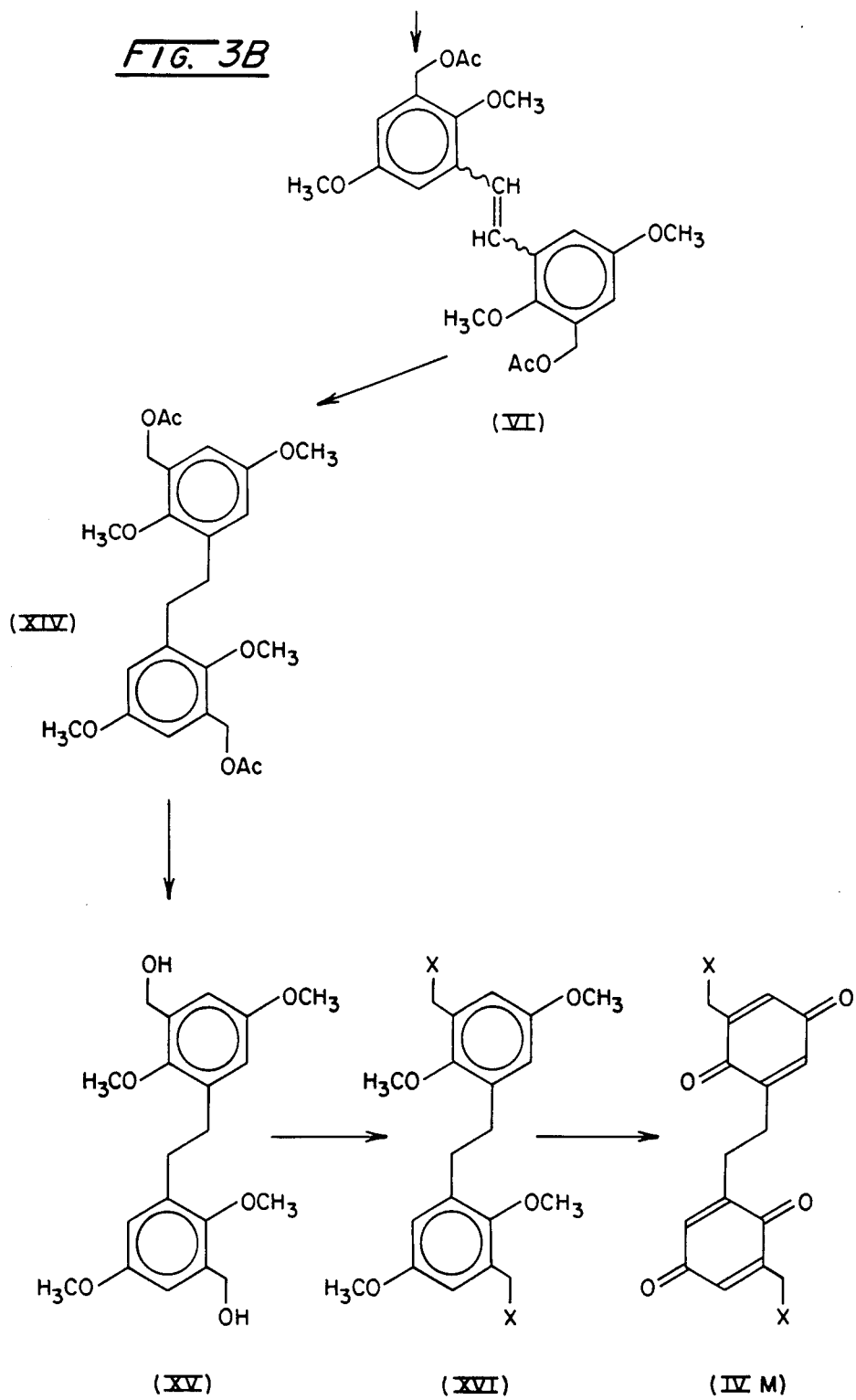

ANTI-CANCER AGENTS AND PROCESSES FOR THEIR PREPARATION

The invention described herein was made in the course of work under Grant 5 R01 CA25445-03 made by the U.S. Department of Health and Human Services. The Government has certain rights in this invention.

This application is a continuation of application Ser. No. 526895, filed Aug. 26, 1983 now abandoned.

BACKGROUND OF THE INVENTION

This invention relates to anti-cancer agents and processes for their preparation. More particularly, it relates to anti-cancer agents which are bis(bioreductive) alkylating agents.

Several known anti-cancer agents having a quinone nucleus owe their antineoplastic properties to their ability to interact with desoxyribonucleic acid (DNA). For example, the mechanism of action of antitumor mitomycins is believed to involve in vivo enzymatic reduction of the quinone nucleus with consequent generation of reactive quinone methides capable of alkylating DNA, ribonucleic acid (RNA) and other biological macromolecules; see, inter alia:

Kennedy et al, Fed. Am. Soc. Exp. Biol., 38,443 (1979); and

Proc. Am. Assoc. Cancer Res., 20, 278 (1979). Some of the antitumor agents seem to act as bifunctional alkylators which add to both strands of the DNA double helix, thereby causing cross-linking; see:

Iyer et al, Proc. Natl. Acad. Sci. U.S., 50, 355 (1963). It is also known that certain bifunctional alkylators not requiring bioreductive activation are more effective than their monofunctional counterparts; see, inter alia:

Pelaprat et al, J. Med. Chem., 23, 1336 (1980); Gaugain et al, Biochemistry, 17, 5071 (1978); and Neidle, in Ellis and West (eds.), Progress in Medicinal Chemistry, 16, 151–221 (Elsevier/North-Holland Biomedical Press, Amsterdam, 1979).

However, according to:

Lin et al, J. Med. Chem., 19, 1336 (1976) when two alkylating chains are bonded to the same quinone ring, the bifunctional alkylators are no more efficient than the corresponding monofunctional alkylators.

After careful consideration, we concluded that the failure of the Lin bifunctional alkylators to show activity greater than that of the corresponding monofunctional alkylators might be due to an improper spacing between the two alkylating groups and accordingly that better results might be obtained using bifunctional alkylators in which a spacer region is interposed between two quinone alkylating moieties. Accordingly, we have now synthesized certain compounds of this type and found that they exhibit highly desirable antitumor activity in animal tests.

SUMMARY OF THE INVENTION

Accordingly, in one aspect this invention provides a compound of Formula I in FIG. 1 of the accompanying drawings wherein $R_1$ and $R_2$ are each a hydrogen atom, or $R_1$ and $R_2$ together form a methylene group, each X is a bromo, iodo or tosyloxy group and the dotted bonds indicate that the central $-CHR_1-CHR_2-$ linkage is attached to the two phenyl rings at positions which are either meta to both $CH_2X$ groups or para to both $CH_2X$ groups.

In another aspect this invention provides a process for treating an animal suffering from cancer which comprises administering to the animal a therapeutically effective amount of an instant compound of Formula I.

This invention also provides a compound of Formula V shown in the accompanying drawings wherein each Q is a bromo, iodo, tosyloxy, hydroxy or acetyloxy group, the compound of Formula VI shown in the accompanying drawings in the form of its E or Z isomer or a mixture thereof, and a compound of Formula VII shown in the accompanying drawings wherein G is a triphenylphosphonium chloride, chloromethyl, CHO, or hydroxymethyl group. The compounds of Formulae V, VI and VII are intermediates used in preparing certain of the compounds of Formula I.

The invention extends to the processes set forth below for preparing compounds of Formula I.

BRIEF DESCRIPTION OF THE DRAWINGS

FIGS. 3A and 3B shows one method for the synthesis of the compounds of Formula IVM shown in FIG. 1.

DETAILED DESCRIPTION OF THE INVENTION

Figure 1:
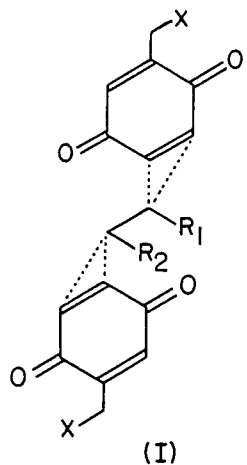
FIG. 1 shows the general Formula I covering all the pharmaceutically active compounds of the invention, together with the formulae of various sub-groups of compounds which fall within Formula I.
Figure 1:
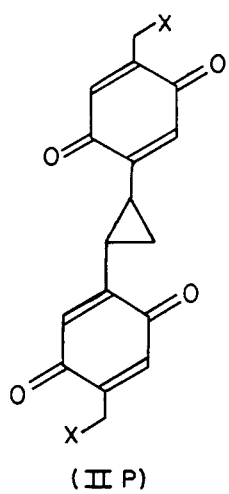
Figure 1:
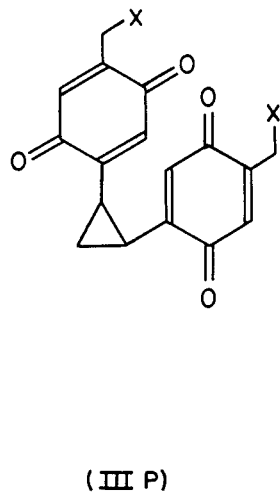
Figure 1:
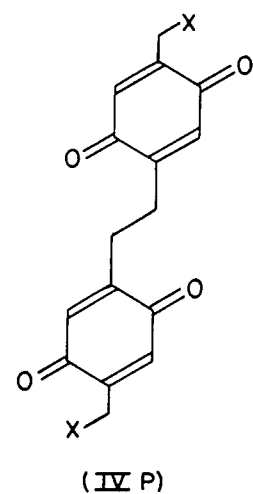
Figure 1:
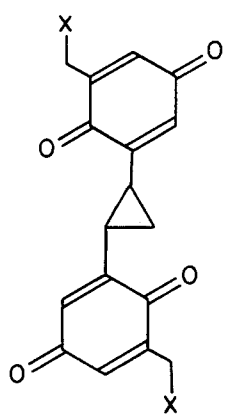
Figure 1:
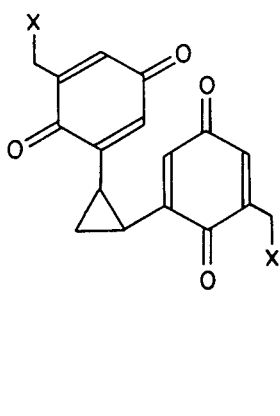
Figure 1:
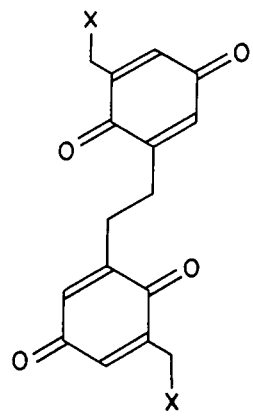
Figure 2:
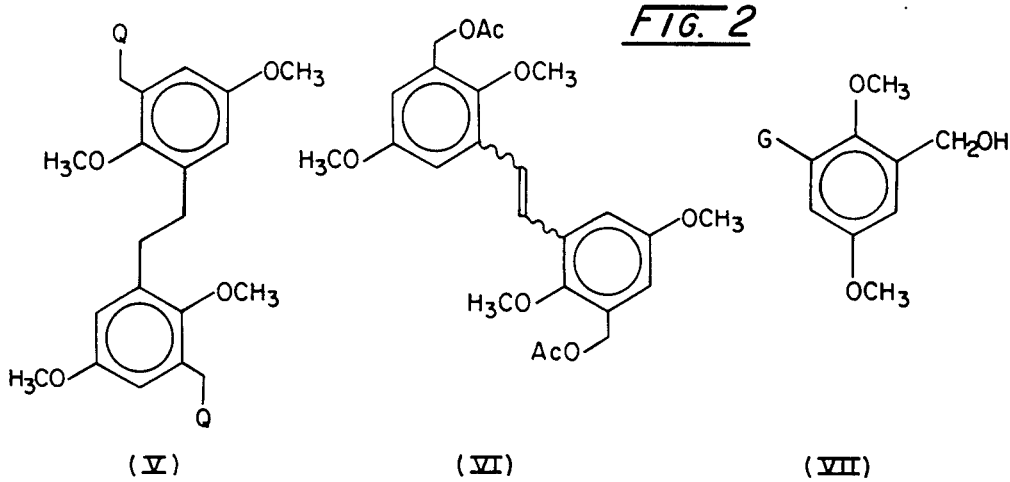
FIG. 2 shows Formulae V, VI and VII of the intermediates used to prepare certain compounds of Formula I.

As already mentioned, the instant anti-cancer agents are the compounds of Formula I (shown in FIG. 1 of the accompanying drawings) wherein $R_1$ and $R_2$ are each a hydrogen atom or $R_1$ and $R_2$ together form a methylene group and each X is a bromo, iodo or tosyloxy group. In Formula I, the dotted bonds indicate that the central $-CHR_1-CHR_2-$ linkage is attached to the two phenyl rings at positions which are either meta to both $CH_2X$ groups or para to both such groups. The compounds of Formula I may conveniently be divided into six sub-groups depending upon the nature of the central $-CHR_1-CHR_2-$ linkage and whether this linkage is meta or para to the $CH_2X$ groups, these six sub-groups of compounds falling within Formula I being represented by Formulae IIM, IIP, IIIM, IIIP, IVM and IVP shown in FIG. 1. The compounds of Formula I in which the central linkage is an E (or trans) cyclopropylene ring are referred to herein as compounds of Formula IIM or IIP depending upon whether the central linkage is meta or para respectively to the $CH_2X$ groups. Similarly, the compounds of Formula I in which the central linkage is a Z (or cis) cyclopropylene ring are designated compounds of Formula IIIM or IIIP, and the compounds in which the central linkage is an ethylene linkage are designated compounds of Formula IVM or IVP respectively. The preferred sub-groups of compounds falling within Formula I are those of Formula IIP, IIIP and IVM. Furthermore, the preferred substituent X is bromine. The most preferred compound of Formula I is the compound of Formula IVM in which each substituent X is a bromine atom, namely 2,2'-ethylenebis[6-(bromomethyl)-p-benzoquinone].

As already mentioned, the compounds of Formula I are useful as anti-cancer agents. For this purpose, the agents should be administered to an animal suffering from cancer, an appropriate mode of administration being intraperitoneal administration. Since the quinones of Formula I are not readily water-soluble, appropriate pharmaceutical compositions for administration of the compounds of Formula I may be prepared by suspending or emulsifying the active compounds in an appropriate aqueous vehicle such as 0.3 percent Klucel. Although the dosage rate at which the compounds of Formula I should be administered will of course vary with the animal and the type of tumor being treated, in general dosage rates will be in the range of about 2 to about 50 mg./day/kilogram body weight.

The exact synthetic route used to prepare the compounds of Formula I varies somewhat depending upon whether the central linkage is a cyclopropylene or ethylene linkage and the relative positions of this linkage and the $CH_2X$ groups. For this reason, the synthesis of each of the six sub-groups of compounds of Formulae IIM, IIP, IIIM, IIIP, IVM and IVP will be considered separately below.

Figure 3A:
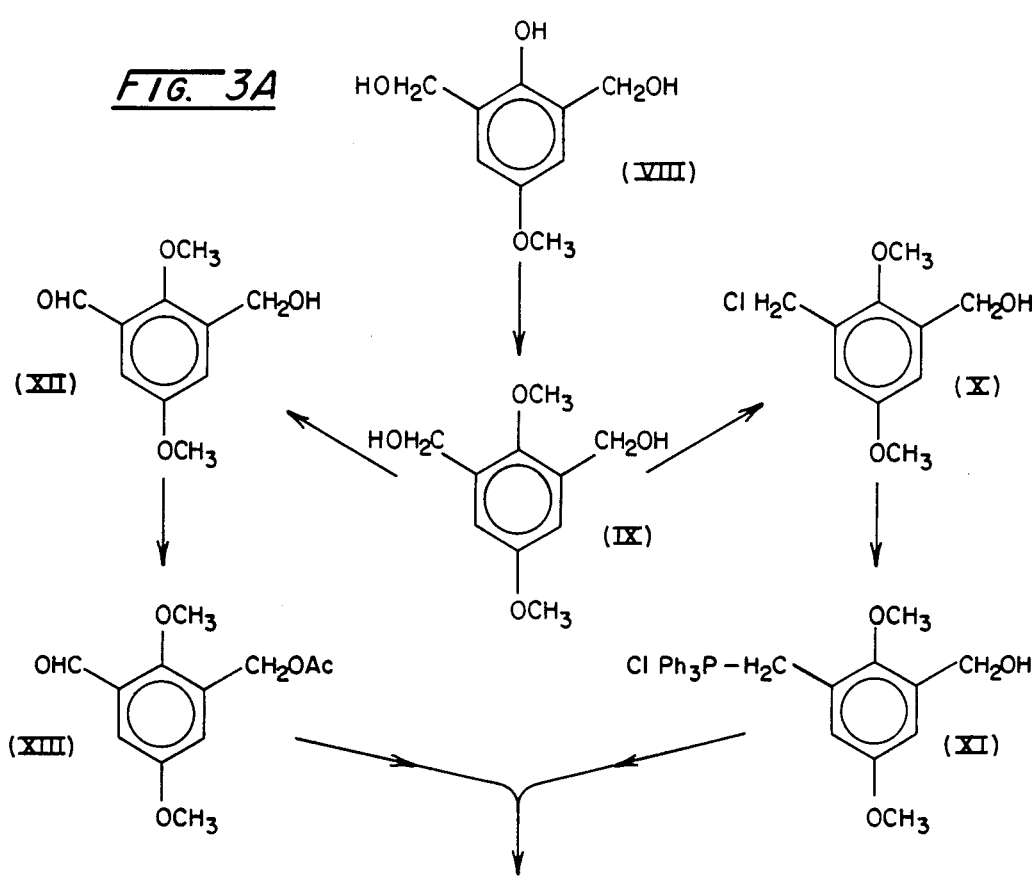

The preferred synthetic route for synthesis of compounds of Formula IVM is shown in FIG. 3 of the accompanying drawings. The synthesis commences with the known compound 2,6-di(hydroxymethyl)-4-methoxyphenol (designated VIII in FIG. 3) which may be prepared as described by Moran et al, J. Am. Chem. Soc., 74, 127 (1952). Although this paper gives a melting point for compound VIII of 127°–128° C., as prepared by us the compound has a melting point of 130°–131° C. In the first step of the synthesis, the phenolic hydroxyl group of compound VIII is methylated, preferably with an excess of methyl iodide in acetone, to produce 1,3-di(hydroxymethyl)-2,5-dimethoxybenzene (designated IX in FIG. 3; this is the compound of Formula VII in which G is a hydroxymethyl group).

One portion of the compound IX is next treated to replace one of its free hydroxyl groups with a chlorine atom, thereby producing 3-(chloromethyl)-2,5-dimethoxybenzyl alcohol (designated X in FIG. 3; this is the compound of Formula VII in which G is a chloromethyl group). The conversion of IX to X is conveniently effected with concentrated hydrochloric acid in an aromatic hydrocarbon such as benzene. Reaction of compound X with triphenylphosphine produces [2,5-dimethoxy-3-(hydroxymethyl)benzyl]triphenylphosphonium chloride (designated XI in FIG. 3; this is the compound of Formula VII in which G is a triphenylphosphonium chloride group).

A second portion of compound IX is partially oxidized to the corresponding monoaldehyde, 2,5-dimethoxy-3-(hydroxymethyl)benzaldehyde (designated XII in FIG. 3; this is the compound of Formula VII in which G is a —CHO group). This partial oxidation may be effected using, inter alia, pyridinium chlorochromate in acetone or manganese dioxide in acetone. The compound XII is then acetylated using, for example, acetic anhydride in pyridine, to produce the corresponding acetate, 3-(acetyloxy)-methyl-2,5-dimethoxybenzaldehyde (designated XIII in FIG. 3).

Compounds XI and XIII are then condensed with one another and the product acetylated to yield a mixture of the Z and E isomers of 1,2-bis[3-[(acetyloxy)methyl]-2,5-dimethoxyphenyl]ethane, the compound of Formula VI. The condensation is conveniently effected by dissolving a mixture of the phosphonium salt XI and sodium hydride in benzene at room temperature then adding the aldehyde XIII. The condensation product may then be acetylated with acetic anhydride in pyridine. The two isomers may be separated by chromatography on silica gel and elution with a 12 percent ethyl acetate/88 percent hexane mixture, followed by trituration with a 1:1 benzene/hexane mixture.

The Z (or cis) isomer of coompound VI is next reduced to produce 1,2-bis[3-[(acetyloxy)methyl]-2,5-dimethoxyphenyl]ethane (designated XIV in FIG. 3; this is the compound of Formula V in which Q is an acetyloxy group). The preferred reagent for this reduction is sodium borohydride/cobaltous chloride which effects the reduction substantially quantitatively. Hydrolysis of XIV yields the corresponding diol, 1,2-bis[3-(hydroxymethyl)-2,5-dimethoxyphenyl]ethane (designated XV in FIG. 3; this is the compound of Formula V in which Q is a hydroxy group). The hydrolysis is conveniently effected using a methanolic solution of an alkali metal hydroxide, this solution containing a small proportion of water.

The next and penultimate step of the synthesis is the conversion of the two hydroxyl groups in compound XV to the appropriate groups X, thereby producing a compound of Formula XVI in FIG. 3 (this being a compound of Formula V in which Q is a bromo, iodo or tosyloxy group). The exact method used to insert the groups X will of course vary with the desired group X. When each X is to be a bromine atom, conversion of XV to the corresponding dibromo compound of Formula XVI may be accomplished by treatment with phosphorous tribromide or thionyl bromide. Insertion of tosyloxy groups X may be achieved by treating XV with tosyl chloride. Alternatively, the tosyloxy compound of Formula XVI might be prepared by transesterification of XIV. Iodo compounds of Formula XVI may be prepared either by treating XV with a mixture of iodine and red phosphorous or, more satisfactorily, by first converting XV to its bis(benzyl ether) and then treating this bisether with iodotrimethylsilane.

Finally, the appropriate tetramethoxy compound of Formula XVI is oxidized to produce the bisquinone of Formula IVM. The preferred reagent for carrying out this oxidation is ceric ammonium nitrate; it appears the silver oxide is not effective in carrying out this oxidation either in the presence of weak organic acids such as pyrazine-2,3-dicarboxylic acid or in the presence of mineral acids such as phosphoric acid.

Obviously, the compounds of Formula IVP can be prepared in an exactly analogous manner using as the starting material 2,5-di(hydroxymethyl)-4-methoxyphenol in place of the 2,6-isomer VIII. However, it should be noted that the compound XXIII, which is the regioisomer of compound VI needed to prepare the compounds of Formula IVP by a series of steps exactly analogous to that by which the compounds of Formula IVM are prepared from compound VI, may also be prepared as described below with reference to the synthesis of compounds of Formula IIP.

Figure 4A:
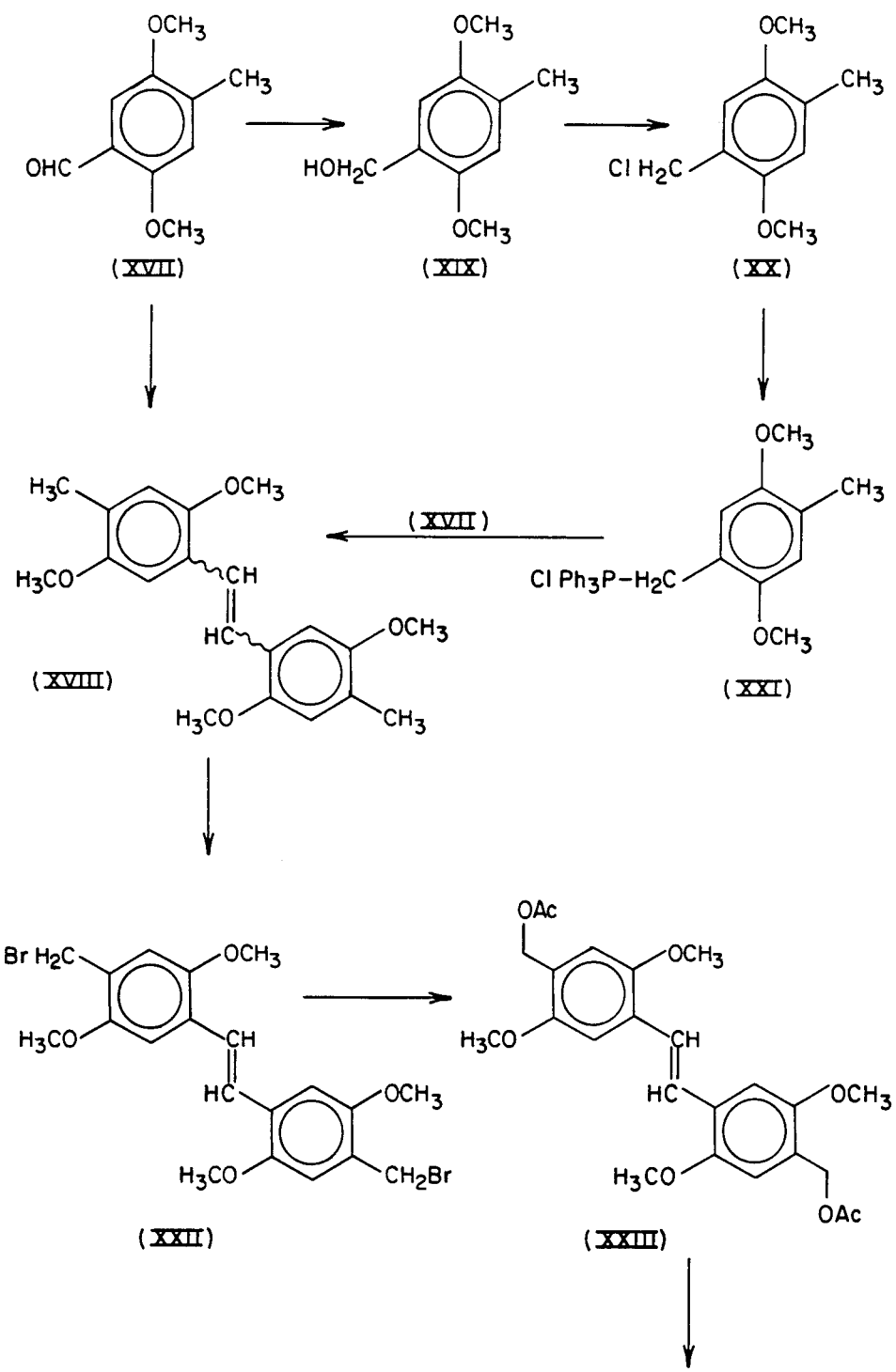
FIGS. 4A and 4B shows the method used for the synthesis of the compounds of Formula IIP shown in FIG. 1.
Figure 4B:
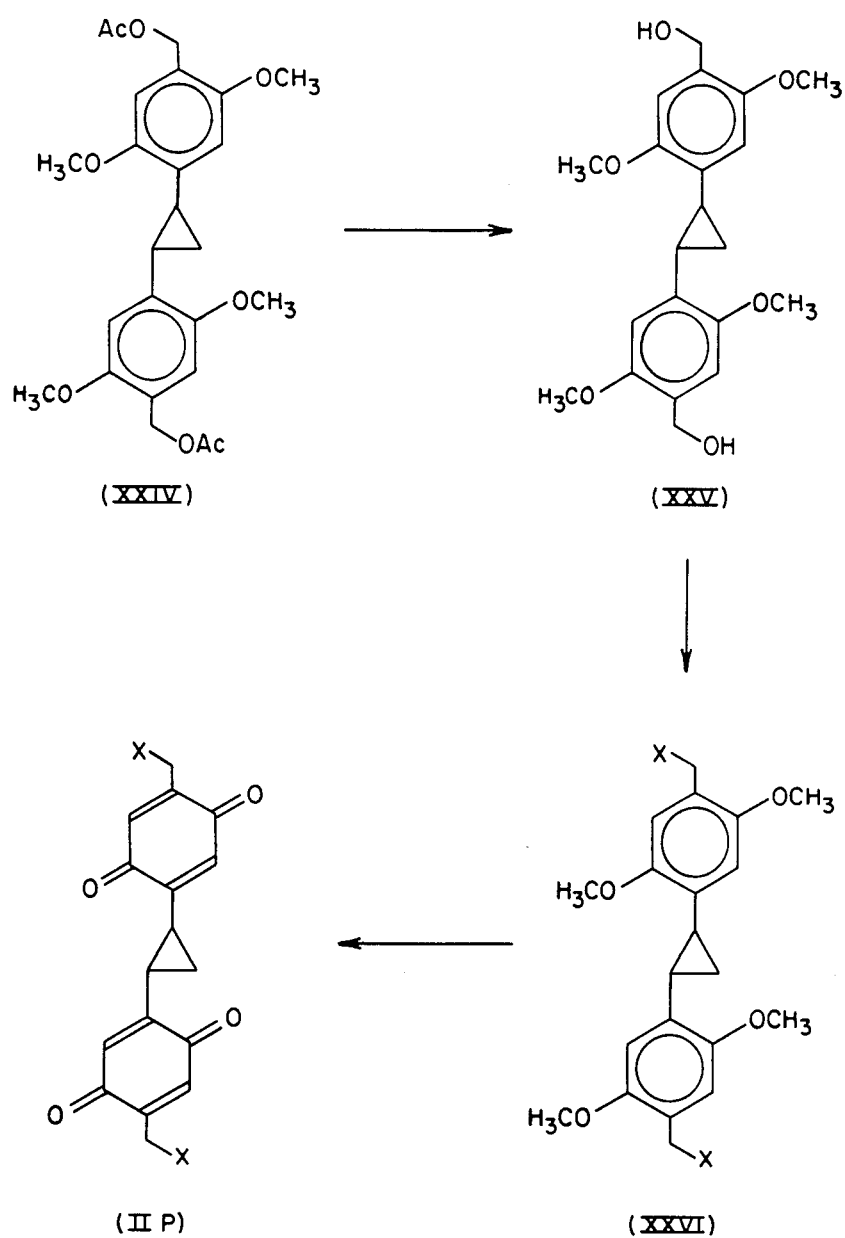

The synthetic route used to prepare compounds of Formula IIP is shown in FIG. 4. As illustrated in that Figure, although several variations of the synthesis are possible all begin from 2,5-dimethoxy-4-methylbenzaldehyde, compound XVII, which was prepared by the method described in Standridge et al, J. Med. Chem,, 19, 1400 (1976). Although this paper gives a melting point of 77°–78° C. for this compound, as prepared by us the compound had a melting point of 80°-82° C. The aldehyde XVII can be converted directly to the E (or trans) isomer of 1,2-bis(2,5-dimethoxy-p-tolyl)ethane (the E isomer of the compound designated XVIII in FIG. 4) by treatment with lithium metal and titanium tetrachloride in dimethoxyethane, but the maximum yield we have been able to obtain by this direct route is only about 34 percent. Accordingly, we prefer to first reduce compound XVII to the corresponding alcohol XIX then convert the alcohol XIX to the corresponding chloromethyl compound XX, both reactions being carried out as described in the aforementioned Standridge et al. paper. Treatment of the chloromethyl compound XX with triphenylphosphine yields (2,5-dimethoxy-4-methylbenzyl)triphenylphosphonium chloride (designated XXI in FIG. 4). Condensation of this phosphonium salt XXI with the aldehyde XVII yields a separable mixture of the E and Z isomers of compound XVIII, this condensation reaction of course being very similar to that by which compound VI is prepared by condensation of XI with XIII, as described above with reference to FIG. 3.

To prepare a compound of Formula IIP, the E-isomer of XVIII is first brominated on both methyl groups to produce (E)-1,2-bis[4-[(acetyloxy)methyl]-2,5-dimethoxyphenyl]ethane (designated XXII in FIG. 4; this bromination is conveniently effected using N-bromosuccininide with 2,2'-azobis(2-methylpropionitrile) as catalyst. The dibromo compound XXII is then acetylated, conveniently by treatment with an anhydrous potassium acetate/acetic acid mixture, to yield the corresponding diacetate, (E)-1,2-bis[4-[(acetyloxy)methyl]-2,5-dimethoxyphenyl]ethane (designated XXIII in FIG. 4). The diacetate XXIII is then cyclopropanated, conveniently by treatment with ethyl iodide in the presence of a zinc/copper couple (see Smith et al, Org. Synth., Coll. Vol., 5, 855-858 (1973)), to produce (E)-1,2-bis[4-[(acetyloxy)methyl]-2,5-dimethoxyphenyl]cyclopropane, (designated XXIV in FIG. 4).

The remaining steps of the synthesis are essentially similar to the conversion of the compound XIV to compounds of Formula IVM, as described above with reference to FIG. 3 The diacetate XXIV is hydrolyzed to the corresponding diol XXV and the groups X inserted in any of the ways previously described for conversion of the diol XV to the corresponding di-X compound XVI as described above thereby producing a compound of Formula XXVI. Finally, the tetramethoxy compound XXVI is demethylated and oxidized to the bisquinone of Formula IIP. However, the reagents needed for the oxidation of a compound of Formula XXVI to the corresponding compound of Formula IIP are different from those required to convert a compound of Formula XVI to the corresponding compound of Formula IVM; ceric ammonium nitrate is not effective to oxidize the compounds of Formula XXVI and instead it is preferred that the compound can be oxidized electrochemically in methanolic potassium hydroxide using platinum electrodes. This electrochemical oxidation converts the compound of Formula XXVI to the bisketal of the bisquinone, and this bisketal is readily hydrolyzed, for example with hydrochloric acid, to the free bisquinone.

Obviously, the compounds of Formula IIIP can be prepared in an exactly analogous manner but using the Z-isomer of XXII instead of the E-isomer thereof. Also, the compounds of Formulae IIM and IIIM can similarly be prepared from the E- and Z-isomers respectively of compound VI.

It will be apparent to those skilled in the art that numerous other methods exist which will produce compounds of Formula I. Thus, this invention extends to the compounds of Formula I, and the intermediates of Formulae V, VI and VII per se and is not restricted to any particular method of preparation of these compounds.

The following examples are now given, though by way of illustration only, to show details of particularly preferred compounds, methods of use and methods of synthesis of the instant compounds.

EXAMPLE I

Preparation of 1,3-di(hydroxymethyl)-2,5-dimethoxybenzene

This example illustrates the preparation of the compound IX, which is also the compound of Formula VII wherein G is a hydroxymethyl group.

2,6-Di(hydroxymethyl)-4-methoxyphenol (VIII) was prepared by the procedure described in Moran et al, J. Am. Chem. Soc., 74, 127 (1952) and had a melting point of 130°-131°. 0.92 g. (5.0 mmole) of VIII, 0.69 g. (5.0 mmole) of potassium carbonate and 1 ml. (16.1 mmole) of methyl iodide were dissolved in 30 ml. of acetone and refluxed. This refluxing was continued for two days, three further additions of 1 ml. of methyl iodide being made during the refluxing. Thereafter, the reaction mixture was filtered and the filtrate evaporated to dryness in vacuo. The residue was extracted with hot ethyl acetate, the resultant solution filtered and the solvent removed in vacuo to produce 0.89 g. (90% of theoretical) of 1,3-di(hydroxymethyl)-2,5-dimethoxybenzene (IX) as a colorless solid. Recrystallization from a mixture of ethyl acetate and hexane afforded the pure compound, melting point 106°-108°. The infrared spectrum showed a broak peak at 3200 cm$^{-1}$, while the proton nuclear magnetic resonance (PNMR) in deuterochloroform at room temperature showed peaks at delta=2.05 (broad singlet, 2 protons, exchangeable with deuterium oxide and attributed to the hydroxyl protons), 3.80 (singlet, 6 protons, attributed to methoxy protons), 4.70 (broad singlet, 4 protons, attributed to methylene protons) and 6.88 (singlet, 2 protons, attributed to aromatic protons) ppm. The mass spectrum showed a parent ion at m/e 198 in agreement with the formula $C_{10}H_{14}O_4$.

EXAMPLE II

Preparation of 3-(chloromethyl)-2,5-dimethoxybenzyl alcohol

This example illustrates the preparation of the compound X, which is also the compound of Formula VII in which G is a chloromethyl group.

7.1 g. (35.9 mmole) of IX, prepared as described in Example I above were suspended with stirring in 150 ml. of benzene and 20 ml. of concentrated hydrochloric acid were added. The resultant clear solution was stirred overnight at room temperature, then washed with brine and the aqueous layer extracted with methylene chloride. The organic layer was dried over potassium chloride and the solvent removed in vacuo to yield 7.76 g (100% of theoretical) of 3-(chloromethyl)-2,5-dimethoxybenzyl alcohol (X) as a light brown oil which solidified on standing. Two recrystallizations from a mixture of ethyl acetate and hexane provided the pure compound as long colorless needles, melting point 48°-50° C. The infrared spectrum showed peaks at 3245, 3140, 1610 and 1480 cm$^{-1}$, while the PNMR spectrum in deuterochloroform at room temperature showed peaks at delta=2.31 (broad singlet, one proton, exchangeable with deuterium oxide, attributed to hydroxyl protons), 3.79 (singlet, 3 protons attributed to methoxy protons), 3.83 (singlet, 3 protons, attributed to methoxyprotons), 4.62 (singlet, 2 protons, attributed to chloro methyl protons), 4.69 (singlet, 2 protons, attributed to CH$_2$O protons) and 6.89 (double doublet, 2 protons, J=3.2 and 6.0 Hz, attributed to aromatic protons) ppm. The mass spectrum showed a parent ion at m/e 216 in agreement with the formula C$_{10}$H$_{13}$O$_3$Cl.

EXAMPLE III

Preparation of [2,5-dimethoxy-3-(hydroxymethyl)benzyl]triphenylphosphonium chloride This example illustrates the preparation of the compound of Formula XI, which is also the compound of Formula VII in which G is a triphenylphosphonium chloride group.

7.43 g. (34.3 mmole) of X, prepared as described in Example II above) and 10.8 g. (41.2 mmole) of triphenylphosphine were dissolved in 100 ml. of benzene, refluxed for 18 hours and then cooled. The resultant precipitate was filtered off, washed with benzene and dried under reduced pressure to yield 13.89 g. of a white solid. Treatment of the filtrate with 1.0 g. of fresh triphenylphosphine for two days afforded an additional 1.5 g. of the same white solid for a combined yield of 15.39 g. (94% of theoretical). Recrystallization of the white solid from a methanol/acetone mixture produced colorless, transparent prisms, melting point 230°-232° C.

EXAMPLE IV

Preparation of 2,5-dimethoxy-3-(hydroxymethyl)benzaldehyde

This example illustrates two methods for the preparation of the compound of Formula XII, which is also the compound of Formula VII in which G is a —CHO group.

(a) Oxidation with pyridinium chlorochromate 10 g. (50.5 mmole) of IX, prepared as described in Example I above, were dissolved in 1 l. of acetone and the resultant solution cooled in ice. 10.9 g. (50.6 mmole) of solid pyridinium chlorochromate were then added to the ice-cold solution which was then allowed to stand for 15 minutes. The solution was allowed to warm to room temperature and stirred at room temperature for 2.5 hours. 50 ml. of water was then added to the solution which was then evaporated to 150 ml. under reduced pressure and extracted with ethyl acetate. The ethyl acetate layer was washed with two 250 ml. aliquots of water and saturated brine and dried over potassium carbonate. Finally, the solvent was removed in vacuo to give 9.45 g. of an orange solid.

Chromatography of this solid on silica gel using a hexane/ethyl acetate mixture as eluant resolved the orange solid into three components. A 95:5 v/v hexane/ethyl acetate mixture first eluted 2,5-dimethoxy-1,3-benzenedicarboxaldehyde. Further elution with a 85:15 hexane/ethyl acetate mixture first eluted 2,5-dimethoxy-3-(3-oxo-1-butenyl)benzaldehyde, and then the desired, 2,5-dimethoxy-3-(hydroxymethyl)benzaldehyde, the desired compound being recovered in an amount of 6.15 g. (62 percent of theoretical). Recrystallization of the desired product from ethyl acetate/hexane yielded colorless needles, melting point 74°-76° C.

The infrared spectrum of the recrystallized product showed a broak peak at 3260 cm$^{-1}$ and other peaks at 1695, 1600, 1590 and 1475 cm$^{-1}$ The PNMR spectrum in deutrochloroform at room temperature showed peaks at delta=2.20 (triplet, 1 proton, J=4.8 Hz, exchangeable with deuterium oxide, attributed to hydroxyl proton), 3.83 (singlet, 3 protons, attributed to methoxy protons), 3.90 (singlet, 3 protons, attributed to methoxy protons), 4.73 (doublet, 2 protons, J=4.8 Hz, attributed to methylene protons), 7.25 (singlet, 2 protons, attributed to aromatic protons) and 10.32 (singlet, 1 proton, attributed to CHO proton) ppm. The mass spectrum showed a parent ion at m/e 196, in agreement with the formula of C$_{10}$H$_{12}$O$_4$.

(b) Oxidation with manganese dioxide 1.0 g (5.1 mole) of IX prepared as described in Example I was dissolved in 50 ml. of acetone (chloroform may alternatively be used) and 1.09 g (12.5 mole) of active manganese dioxide was added. The resultant mixture was stirred at room temperature for 24 hours, after which time filtration and evaporation of the filtrate on a rotary evaporator afforded a mixture of the desired produce XII and the starting material; the mixture was estimated by PNMR to be approximately 60:40. The pure compound XII was isolated by chromatography on silica gel using an 85:15 v/v hexane/ethyl acetate mixture as the eluant.

EXAMPLE V

Preparation of 3-(acetyloxy)methyl-2,5-dimethoxybenzaldehyde

This example illustrates the preparation of the compound of Formula XIII.

5.6 g. of 2,5-dimethoxy-3-(hydroxymethyl)benzaldehyde, prepared as described in Example IVa or IVb above, were dissolved in a mixture of 10 ml. of dry pyridine and 5 ml. of acetic anhydride at room temperature and the resultant solution stirred overnight at room temperature. The resultant reaction mixture was extracted with ether, dried and the ether removed to produce a colorless oil having boiling point of 140°-144° C. (bath temperature) at 0.5 mm. Hg. pressure. The infrared spectrum in carbon tetrachloride showed peaks at 1750, 1700, 1610, 1595, 1485 and 1125 cm.$^{-1}$, while the PNMR spectrum in deutrochloroform showed peaks at delta=2.13 (singlet, 3 protons, attributed to protons in the OCOCH$_3$ group), 3.83 (singlet, 3 protons, attributed to methoxy protons), 3.91 (singlet, 3 protons, attributed to methoxy protons), 5.19 (singlet, 2 protons, attributed to methylene protons), 7.26 (double doublet, 2 protons, J=3.2 and 8.0 Hz, attributed to aromatic protons) and 10.35 (singlet, 1 proton, attributed to CHO proton) ppm.

EXAMPLE VI

Preparation of 1,2-bis[3-[(acetyloxy)methyl]-2,5-dimethoxyphenyl]ethene

This example illustrates the preparation of the Z and E isomers of the compound of Formula VI.

5.56 g. of a 50 percent slurry (116 mmole) of sodium hydride were added to a stirred suspension of 13.89 g. (29 mmole) of XI (prepared as described in Example III above) in 100 ml. of benzene at room temperature under a nitrogen atmosphere. The resultant yellow mixture was refluxed for two hours, then cooled and 6.9 g. (29 mmole) of XIII, prepared as described in Example V above, were added. Refluxing, with stirring, was continued overnight, then the reaction mixture was cooled, excess sodium hydride decomposed by the addition of methanol and the reaction mixture poured over crushed ice and extracted with methylene chloride. The organic layer was washed with water and dried over sodium sulfate, then concentrated under reduced pressure to give 18.5 g. of a light brown oil. This oil was dissolved in 25 ml. of pyridine and 20 ml. of acetic anhydride were added. The mixture was stirred overnight at room temperature then poured over an ice/water mixture and re-extracted with methylene chloride, the organic phase being washed with water, dried over sodium sulfate and the solvent then being removed. The resultant 20.5 g of crude acetylated product was chromatographed on silica gel, the paraffin oil impurity in the crude product (derived from the original unwashed sodium hydride slurry), was removed by elution with hexane. Subsequent elution with a 12:88 v/v ethyl acetate/hexane mixture yielded 7.20 g. (56 percent of theoretical) of (Z)-1,2-bis[3-[(acetyloxy)methyl]-2,5-dimethoxy-phenyl]ethene as a colorless liquid, which, without distillation, gave a proper elemental analysis. Further elution with the same eluant yielded 1.80 g. of a mixture of the Z- and E-isomers of the same compound in which the Z-isomer predominated. The infrared spectrum of this Z isomer in carbon tetrachloride showed peaks at 1750, 1610, 1475 and 1230 cm$^{-1}$, while the PNMR spectrum in deutrochloroform showed peaks at delta=2.12 (singlet, 6 protons, attributed to OCOCH$_3$ protons), 3.55 (singlet, 6 protons, attributed to methoxy protons), 3.80 (singlet, 6 protons, attributed to methoxy protons), 5.14 (singlet, 4 protons, attributed to methylene protons), 6.69 (doublet, 2 protons, J=2.9 Hz., attributed to aromatic protons) and 6.79 (doublet, 4 hydrogens, J=2.9 Hz., attributed to aromatic and ethylenic protons) ppm. The mass spectrum showed a parent ion at m/e 444 in agreement with the formula $C_{24}H_{28}O_8$.

Finally, further elution with a 13:78 v/v ethyl acetate/hexane mixture yielded 0.6 g. (5% of theoretical) of the pure E-isomer, which, after solvent removal, appeared as white needles, melting point 149°–151° C. The infrared spectrum of this compound showed peaks at 1530, 1610, 1595, 1485 and 955 cm$^{-1}$, while its PNMR spectrum in deuterochloroform showed peaks at delta=2.15 (singlet, 6 protons, attributed to OCOCH$_3$ protons), 3.77 (singlet, 6 protons, attributed to methoxy protons), 3.84 (singlet, 6 protons, attributed to methoxy protons), 5.18 (singlet, 4 protons, attributed to methylene protons), 6.87 (doublet, 2 protons, J=3.1 Hz., attributed to aromatic protons), 7.15 (doublet, 2 protons, J=2.9 Hz., attributed to aromatic protons) and 7.35 (singlet, 2 protons, attributed to ethylenic protons) ppm.

Although the above procedure for the synthesis of VI is preferred since it yields the Z isomer required for the later steps in the synthesis of compounds of Formula IVM (the E-isomer being very difficult to reduce to XIV), if only the E-isomer is desired for the reactions, described above, for preparing other compounds of Formula I, the E-isomer may be prepared by the following alternative route. Compound VIII is converted to 2,5-dimethoxy-3-methylbenzyl alcohol (boiling point 112°–115° C. at 0.65 mm. Hg.) by the procedure described in Nichols et al, J. Med. Chem., 17, 161 (1974) and this alcohol in turn is converted to 2,5-dimethoxy-3-methylbenzyl chloride by the procedure described in the aforementioned paper by Standridge et al. Reaction of the chloride with triphenylphosphine in benzene produces the corresponding triphenylphosphonium chloride (melting point 220°–223° C.), whic may be converted to (E)-1,2-bis(2,5-dimethoxy-m-tolyl)ethene by reaction with a lithium/bromobenzene mixture in anhydrous dimethyl ether. This compound has a melting point of 138°–140° C., displays peaks in the infrared spectrum at 1590, 1465 and 970 cm$^{-1}$ and peaks in the PNMR spectrum at delta=2.30, 3.72, 3.82, 6.68, 7.02 and 7.36 ppm. Its mass spectrum shows a parent ion at m/e 328 in agreement with the expected formula. Conversion of the tolyl compound to the E-isomer of compound VI may be achieved using N-bromosuccinimide with benzoyl peroxide in carbon tetrachloride. The E-isomer of compound VI may also be prepared by treating 3-(acetyloxy)methyl-2,5-dimethoxybenzaldehyde, prepared as described in Example V above, with a mixture of lithium metal and titanium tetrachloride in dimethoxyethane, working under a nitrogen atmosphere.

EXAMPLE VII

Preparation of 1,2-bis[3-[(acetyloxy)methyl]-2,5-dimethoxyphenyl]ethane

This example illustrates the preparation of compound XIV.

5.0 g (11.2 mmole) of (Z)-1,2-bis[3-[(acetyloxy)methyl]-2,5-dimethoxyphenyl]ethene, prepared as described in Example VI above, were dissolved in a mixture of 40 ml. of anhydrous THF and 80 ml. of absolute ethanol. The solution was cooled to 0° C. and 1.45 g. (11.2 mmole) of anhydrous CoCl$_2$ was added. The resultant mixture was placed under a nitrogen atmosphere, stirred and 1.07 g. (28.3 mmole) of solid sodium borohydride was added. After ten minutes the ice bath used for cooling was removed and the reaction mixture stirred at room temperature overnight and then poured over 100 ml. of cold 3N hydrochloric acid. The resultant solution was extracted with methylene chloride, and the methylene chloride layer was washed with water and dried over sodium sulfate. Concentration of the dried solution under reduced pressure yielded 5.0 g. (100% of theoretical) of 1,2-bis[3-[(acetyloxy)methyl]-2,5-dimethoxyphenyl]ethane as a colorless solid. This product was recrystallized from an ethyl acetate/hexane mixture to give colorless needles, melting point 100°–102° C. The infrared spectrum of the compound displayed peaks at 1730, 1615, 1600 and 1480 cm$^{-1}$, while its PNMR spectrum in deuterochloroform showed peaks at delta=2.12 (singlet, 6 protons, attributed to OCOCH$_3$ protons), 2.92 (singlet, 4 protons, attributed to methylene protons), 3.76 and 3.77 (2 overlapping singlets, 12 protons, attributed to methoxy protons), 5.16 (singlet, 4 protons, attributed to OCH$_2$ protons) and 6.76 (singlet, 4 protons, attributed to aromatic protons) ppm. The mass spectrum of the compound showed a parent ion at m/e 446, in agreement with the formula $C_{24}H_{30}O_8$.

EXAMPLE VIII

Preparation of 1,2-bis[3-(hydroxymethyl)-2,5-dimethoxyphenyl]ethane

This example illustrates the preparation of the compound XV, which is also the compound of Formula V in which Q is a hydroxy group.

2.0 g. (4.5 mmole) of 1,2-bis[3-[(acetyloxy)methyl]-2,5-dimethoxyphenyl]ethane, prepared as described in Example VII above were dissolved in 50 ml. of methanol and cooled in an ice bath. A solution of 0.4 g. (10 mmole) of sodium hydroxide in 1 ml. of water and 10 ml. of methanol was added dropwise and the resultant mixed solution stirred at room temperature overnight, concentrated in vacuo and extracted with methylene chloride. The organic layer was washed with water, dried over sodium sulfate and concentrated in vacuo to yield 1.55 g. (96 percent of theoretical) of 1,2-bis[3-(hydroxymethyl)-2,5-dimethoxyphenyl]ethane as a colorless solid. Recrystallization from a mixture of ethyl acetate and hexane gave light needles, melting point 112°–114° C. The infrared spectrum of the compound showed broad peaks at 3300 and 3120 cm$^{-1}$ and other peaks at 1605 and 1470 cm$^{-1}$. The PNMR spectrum of the compound in deutrochloroform showed peaks at delta=2.05–2.32 (broad multiplet, 2 protons, exchangeable with deuterium oxide, attributed to hydroxyl protons), 2.90 (singlet, 4 protons, attributed to methylene protons), 3.76 and 3.77 (two overlapping singlets, 12 protons, attributed to methoxy protons), 4.72 (singlet, 4 protons, attributed to OCH$_2$ protons), 6.70 (doublet, 2 protons, J=3.2 Hz., attributed to aromatic protons) and 6.79 (doublet, 2 protons, J=2.9 Hz., attributed to aromatic protons) ppm. The mass spectrum showed a parent ion at m/e 362, in agreement with the formula $C_{20}H_{26}O_6$.

EXAMPLE IX

Preparation of 1,2-bis[3-(bromomethyl)-2,5-dimethoxyphenyl]ethane

This example illustrates the preparation of the compound of Formula XVI in which X is a bromine atom, this also being the compound of Formula V in which Q is a bromine atom.

1.27 g. (3.5 mmole) of 1,2-bis[3-(hydroxymethyl)-2,5-dimethoxyphenyl]ethane, prepared as described in Example VIII above, were dissolved in 25 ml. of anhydrous THF. To this solution was added dropwise 0.77 g. (2.8 mmole) of phosphorous tribromide. After standing for ten minutes, the reaction mixture was allowed to warm to room temperature and then stirred overnight. Extraction with methylene chloride and solvent removal in vacuo yielded crude 1,2-bis[3-(bromomethyl)-2,5-dimethoxyphenyl]ethane as a sticky colorless solid. The crude product was purified by chromatography over silica gel using methylene chloride as the eluant to give 1.45 g. (85 percent of theoretical) of the pure compound which crystallized from ethyl acetate as light flakes, melting point 158°–161° C. The infrared spectrum of the compound displayed peaks at 1610, 1590 and 1480 cm$^{-1}$, while its PNMR spectrum in deuterochloroform showed peaks at delta=2.90 (singlet, 4 protons, attributed to methylene protons), 3.76 (singlet, 6 protons, attributed to methoxy protons), 3.85 (singlet, 6 protons, attributed to methoxy protons), 4.56 (singlet, 4 protons, attributed to bromomethyl protons), 6.71 (doublet, 2 protons, J=3.2 Hz., attributed to aromatic protons) and 6.79 (doublet, 2 protons, J=2.9 Hz., attributed to aromatic protons) ppm. The mass spectrum of the compound showed a parent ion at m/e 488, in agreement with the formula $C_{20}H_{24}O_4Br_2$.

EXAMPLE X

Preparation of 2,2'-ethylenebis[6-(bromomethyl)-p-benzoquinone]

This example illustrates the preparation of the compound of Formula IVM in which each X is a bromine atom.

0.85 g. (1.7 mmole) of 1,2-bis[3-(bromomethyl)-2,5-dimethoxyphenyl]ethane, prepared as described in Example IX above, was dissolved in 50 ml. of hot acetonitrile. This solution was cooled to a temperature just above the point at which it became cloudy and then there was added dropwise thereto a solution of 6.37 g. (11.6 mmole) of ceric ammonium nitrate in 8 ml. of water. Stirring of the mixed solution was continued for ten minutes after the addition of the ceric ammonium nitrate was complete, then the reaction mixture was diluted with water and extracted with methylene chloride. The organic extract was washed with water, dried over sodium sulfate and the solvent removed in vacuo to yield 0.75 g. of a dark brown solid. Trituration of this dark brown solid with a small quantity of ethyl acetate afforded 2,2'-ethylenebis[6-(bromomethyl)-p-benzoquinone] as a yellow-brown solid, the yield being 0.62 g. (83 percent of theoretical). Recrystallization from a mixture of ethyl acetate and hexane gave yellow-brown needles, melting point 146°–147° C. The infrared spectrum of the recrystallized material showed peaks at 1650, 1635 and 1615 cm$^{-1}$, while the PNMR spectrum in deuterochloroform showed peaks at delta=2.72 (singlet, 4 protons, attributed to methylene protons), 4.25 (doublet, 4 protons, J=1.0 Hz., attributed to bromomethyl protons), 6.59 (doublet, 2 protons, J=2.2 Hz., attributed to protons on the quinone rings) and 6.85 (multiplet, 2 protons, attributed to protons on the quinone rings) ppm. The mass spectrum of the compound showed a peak at m/e 348 (M-80 for the formula $C_{16}H_{12}O_4Br_2$).

EXAMPLE XI

Preparation of (E)-1,2-bis(2,5-dimethoxy-p-tolyl)ethane

This example illustrates the direct preparation of the E-isomer of compound XVIII from compound XVII.

4.2 g. (27.2 mmole) of titanium tetrachloride were slurried in 40 ml. of freshly distilled dimethoxyethane (DME) and placed under an argon atmosphere with stirring. 0.5 g. (0.078 gram atom) of lithium wire was added to the slurry and the resultant mixture refluxed with stirring for two hours, then cooled. After cooling, a solution of 1.8 g. (10.0 mmole) of 2,5-dimethoxy-4-methylbenzaldehyde (prepared according to the procedure described in the aforementioned Standridge et al. paper) in 10 ml. of DME was added and the resultant mixture refluxed for a further 16 hours. The mixture was then cooled to room temperature, diluted with an equal volume of 60°–90° C. pertroleum ether and filtered through a pad of 60–100 mesh Florisil on a centered glass funnel. The residue was cautiously quenched by slow addition of methanol and the filtrate concentrate in vacuo. The crude product thus obtained was recrystallized from cyclohexane to yield 0.55 g. (34 percent of theoretical) of (E)-1,2-bis(2,5-dimethoxy-p-tolyl)ethene as yellow crystals, melting point 160°–161° C. The infrared spectrum of the compound showed peaks at 1510, 1465 and 960 cm$^{-1}$, while its PNMR spectrum in deutrochloroform showed peaks at delta=2.22 (singlet, 6 protons, attributed to methyl protons), 3.78 (singlet, 6 protons, attributed to methoxy protons), 3.82 (singlet, 6 protons, attributed to methoxy protons), 6.64 (singlet, 2 protons, attributed to ethylenic protons), 7.02 (singlet, 2 protons, attributed to aromatic protons) and 7.30 (singlet, 2 protons, attributed to aromatic protons) ppm. The mass spectrum of the compound showed a parent ion at m/e 328, in agreement with the formula $C_{20}H_{24}O_4$.

EXAMPLE XII

Preparation of (2,5-dimethoxy-4-methylbenzyl)triphenylphosphonium chloride

This example illustrates the preparation of the compound XXI from the compound XVII via compounds XIX and XX.

2.5-dimethoxy-4-methylbenzaldehyde was converted to 2,5-dimethoxy-4-methylbenzyl alcohol and then to 2,5-dimethoxy-4-methylbenzyl chloride by the procedures described in the aforementioned paper by Standridge et al. 24 g. (0.12 mmole) of the chloride and 37.65 g. (0.14 mmole) at triphenylphosphine were dissolved in 200 ml. of benzene and refluxed for five days. The resulting white precipitate was filtered, washed with benzene, and air-dryed to give 53.0 g. (96 percent of theoretical) of (2,5-dimethoxy-4-methylbenzyl)triphenylphosphonium chloride. Recrystallization from a mixture of methanol and acetone produced colorless prisms, melting point 237°–239° C.

EXAMPLE XIII

Preparation of 1,2-bis(2,5-dimethoxy-p-tolyl)ethane

This example illustrates the preparation of the E- and Z-isomers of compound XVIII by reaction of compounds XVII and XXI.

17 g. (0.11 mmole) of bromobenzene were dissolved in 200 ml. of anhydrous diethyl ether under an argon atmosphere. To this solution was added 1.69 g. (0.24 gram atom) of lithium wire and the resultant mixture was stirred for 0.5 hour at room temperature and the liquid decanted. 50.0 g. (0.11 mmole) of (2,5-dimethoxy-4-methylbenzyl)triphenylphosphonium chloride, prepared as described in Example XII above, was added in small portions to the decanted solution and the resultant mixture stirred at room temperature for four hours. Next, a solution of 19.0 g. (0.11 mmole) of 2,5-dimethoxy-4-methylbenzaldehyde in 300 ml. of diethyl ether was added and the resultant mixture refluxed two days. After excess phenyllithium had been decomposed by addition of water, the reaction mixture was filtered, the solids washed with diethyl ether and the combined filtrates dried over sodium sulfate. Removal of the ether solvent gave 27.5 g. of a yellow solid. Analysis of this solid by PNMR indicated that it was a 65:35 mixture of the Z- and E-isomers of 1,2-bis(2,5-dimethoxy-p-tolyl)ethane. Separation of the isomers was accomplished by repeated recrystallization from ethyl acetate to give 8.25 g. (24 percent of theoretical) of the pure E-isomer, melting point 159°–161° C., identical in all respects with the material prepared in Example XI above. 14.20 g. (41 percent of theoretical) of the pure Z-isomer was obtained from the repeated recrystallization as colorless flakes, melting point 114°–115° C. The infrared spectrum of this Z-isomer showed peaks at 1500 and 1470 cm$^{-1}$, while its PNMR spectrum in deutorchloroform showed peaks at delta=2.17 (singlet, 6 protons, attributed to methyl protons), 3.42 (singlet, 6 protons, attributed to methoxy protons), 3.79 (singlet, 6 protons, attributed to methoxy protons), 6.68 (singlet, 4 protons, attributed to aromatic protons) and 6.72 (singlet, 2 protons, attributed to ethylenic protons) ppm. The mass spectrum of the Z-isomer showed a parent ion at m/e 328, in agreement with the formula $C_{20}H_{24}O_4$.

EXAMPLE XIV

Preparation of (E)-1,2-bis[4-[(acetyloxy)methyl]-2,5-dimethoxyphenyl]ethene

This example illustrates the preparation of compound XXIII from compound XVIII via compound XXII.

0.30 g. (0.9 mmole) of (E)-1,2-bis(2,5-dimethoxy-p-tolyl)ethene, prepared as described in Example XI or Example XIII above, was dissolved in 25 ml. of carbon tetrachloride. To this solution was added 0.32 g. (1.8 mmole) of N-bromosuccinimide and a (small) catalytic amount of 2,2'-azobis(2-methylpropionitrile). The resultant mixture was refluxed for 45 minutes, cooled and filtered to yield crude (E)-1,2-bis[4-(bromomethyl)-2,5-dimethoxyphenyl]ethene. The crude dibromo compound obtained by evaporation of the filtrate was used without further purification in the following step.

The dibromo compound was refluxed for three hours in 20 ml. of acetic acid containing 0.35 g. (3.6 mmole) of anhydrous potassium acetate. The acetic acid was then removed in vacuo and the resultant oil combined with 20 ml. of water and extracted twice with methylene chloride. The combined organic extracts were washed with 5 percent sodium bicarbonate solution, then with water and dried over magnesium sulfate. The solvent was then removed and the resultant product recrystallized from aqueous methanol to give 0.10 g. (27 percent of theoretical) of (E)-1,2-bis[4-[(acetyloxy)methyl]-2,5-dimethoxyphenyl]ethene as yellow crystals, melting point 165°–167° C. The infrared spectrum of the recrystallized material showed a peak at 1740 cm$^{-1}$, while its PNMR spectrum in deutrochloroform showed peaks at delta=2.12 (singlet, 6 protons, attributed to $OCOCH_3$ protons), 3.84 (singlet, 6 protons, attributed to methoxy protons), 3.88 (singlet, 6 protons, attributed to methoxy protons), 5.16 (singlet, 4 protons, attributed to methylene protons), 6.91 (singlet, 2 protons, attributed to ethylenic protons), 7.15 (singlet, 2 protons, attributed to aromatic protons) and 7.42 (singlet, 2 protons, attributed to aromatic protons) ppm.

ANIMAL TESTS

The following test results were carried out using 2,2'-ethylenebis[6-(bromomethyl)-p-benzoquinone], the bromo compound of Formula IVM prepared in Example X above.

Four week old random mated homozygous nude (NU/NU) female athymic mice, obtained from the National Cancer Institute were each injected subcutaneously with 0.5 ml. of rabbit anti-mouse thymocyte serum. Seven days later, each mouse was inoculated subcutaneously with 10 million D98/HR1 cells in phosphate buffered saline. Two weeks after the inoculation, a second injection of 0.5 ml. of rabbit anti-mouse thymocyte serum was administered to each mouse. When the tumors thus induced in the mice were approximately 2–3 ml in diameter, or when the number of mice was sufficient to establish groups, the mice were divided into three groups. Group I, comprising three mice, had-0.01 ml./g. body weight of 0.3 percent Klucel vehicle administered intraperitoneally daily for 14 days, the weight of each mouse being established by individual daily weighing. Thus, Group I served as a control group. Group II, comprising five mice, was treated in the same manner except that 5 mg/kg. of the test compound was suspended in the Klucel vehicle. Group III, comprising three mice, was again treated in the same manner except that the dosage rate was 20 mg/kg of the active compound. Tumor measurements were taken on the first day of administration of the test material and weakly thereafter for four weeks, the tumor mass being obtained by measuring the tumor along the longitudinal and traverse axes of the animal and measuring the height of the tumor above the back. Mean tumor size was determined for each group and statistically evaluated over time, the results being shown in Tables 1 and 2 below.

TABLE 1

| | Dosage mg/kg | Sample Size (n) | Week 0 (baseline)[a] | Week 1 | Week 2 | Week 4 |
|---|---|---|---|---|---|---|
| Group I | 0 (control) | 3 | 6.70 ± 5.13 | 24.60 ± 11.17 | 113.47 ± 87.64 | 619.17 ± 355.75 |
| Group II | 5 | 5 | 8.14 ± 1.73 | 16.62 ± 2.84 | 33.86 ± 6.69 | 122.02 ± 29.74 |
| Group III | 20 | 3 | 11.83 + 1.74 | 12.4 ± 1.96 | 17.07 ± 1.56 | 28.97 ± 2.99 |

[a]Means and standard error of the means $\bar{X}$ ± S.E.M. (in mm$^3$) for four wks.

TABLE 2

Group Means Adjusted (via analysis of covariance) for Baseline Measurements for Three Weeks

| | Week 1 | Week 2 | Week 4 |
|---|---|---|---|
| Group I | 53.89 | 151.58 | 921.26 |
| Group II | 22.32 | 43.20 | 137.03 |
| Group III | 12.54 | 17.52 | 29.69 |

From the data given in Tables 1 and 2, it will be seen that the test compound of Formula IVM greatly reduced the tumor volume in the mice.

In Vitro Pharmaceutical Tests

In vitro tests of the pharmaceutical activity of the same test compounds were conducted using the D98/HR1 cell line in a modified version of the clonogenic assay system used by the Southwest Oncology Group for primary tumor tissue; see Glaser et al, J. Proc. Natl. Acad. Sci. U.S., 74, 2574 (1977);

Sammon et al, N. Engl. J. Med., 298, 1321 (1978);

Glaser et al, Science, 176, 1245 (1972);

Glaser et al, Virology, 69, 132 (1976); and

Hamburger et al, Science, 197, 461 (1977).

Preparations of the known antitumor drugs Velban, DHAD, VP 16, Methotrexate, doxorubicin and cisplatin at appropriate stock concentrations were made in sterile distilled water and stored at −70° C. in 0.2 ml. aliquots. The test compound of Formula IVM was first dissolved in dichloromethane at a concentration of 2.5 micrograms per mililiter, diluted further in 95 percent ethanol and finally diluted to the appropriate concentration in McCoy's 5A medium at 37° C. The D98/HR1 cells were grown as monolayers as described in the aforementioned paper from Virology and cell suspensions prepared from 3–4 day old cultures. The cell concentration was adjusted to 400,000 cells/ml. and the cells exposed to the drugs for one hour at 37° C. Following incubation, the treated cell suspensions were washed twice with Eagles spinner medium containing 10 percent fetal bovine serum, resuspended in plating medium and overlaid on a 3 ml. agar base in 60 mm. Plastic petri dishes at a concentration of 67,000 cells per plate. Two separate experiments A and B were run as set forth in Table 3 below, controls being provided for both experiments.

The agar base used contained 5 percent horse serum, 10 percent fetal calf serum, 0.22 mg/ml. sodium pyruvate, 42 microgram/ml. L-serine, 2 mm glutanamine, 50 microgram/ml. Gentamycin and 0.5 percent washed agar in McCoy's 5A medium. The plating medium, used at a rate of 1.5 ml. per dish, contained 10 percent horse serum, 1.5 U/ml. insulin, 0.2 mM ascorbic acid, 1.5 mM glutamine, 50 microgram/ml. asparagine, 0.200 mg/ml. DEAE dextran and 0.050 mg/ml. Gentamycin in CMRL 1066 medium with 0.3 percent washed agar. The plates were incubated at 37° C. in 4 percent carbon dioxide in air for ten days and examined for colony formation. The results are shown in Table 3 below.

TABLE 3

| Antitumor Drug | Drug Conc. (μg/ml) | Survival[a] | Percent Reduction |
|---|---|---|---|
| EXPERIMENT A | | | |
| Control | None | 1.00 ± 0.27 | 0 |
| Velban | 6.0 | <.01 | >99[b,c] |
| DHAD | 0.1 | 0.33 ± 0.03 | 67[d] |
| VP 16 | 3.0 | 0.30 ± 0.03 | 70[c] |
| Methotrexate | 100. | <.01 | >99[b,c] |
| Methotrexate | 0.3 | 0.40 ± 0.10 | 60[d] |
| Doxorubicin | 0.04 | 0.37 ± 0.10 | 63[c] |
| Cisplatin | 10.0 | 0.03 ± 0.03 | 97[b,c] |
| Cisplatin | 0.2 | 0.40 ± 0.10 | 60[d] |
| EXPERIMENT B | | | |
| Control | None | 1.00 ± 0.25 | 0 |
| Test Compound | 2.68 | 0.91 ± 0.21 | 9 |
| Test Compound | 1.34 | 0.77 ± 0.25 | 23 |
| Test Compound | 0.67 | 0.81 ± 0.31 | 19 |
| Test Compound | 0.2 | 1.00 ± 0.48 | 0 |
| Doxorubicin | 0.4 | <0.1 | >99[b,c] |
| Doxorubicin | 0.04 | 0.18 ± 0.09 | 82[c] |
| Doxorubicin | 0.004 | 0.69 ± 0.26 | 31[d] |

[a]Colony counts obtained from the examination of uniform plate surface areas. Control colony were 300 ± 80 for experiment A and 373 ± 95 for experiment B.
[b]Nearly total lack of cell growth.
[c]Indicates significant colony reduction (p = <0.001).
[d]Indicates significant colony reduction (p = <0.01).
The above experiments show that the instant test compound displayed little antitumor activity in this test.

The compounds similar to the test compound of Formula IVM, but having acetyloxy groups in place of the bromine atoms was also subjected to the same in vivo and in vitro tests as the test compound. Although the results obtained with this acetyloxy compound in vivo were eratic, ranging from significant colony reduction to significant colony increase, the acetyloxy compound revealed little or no antitumor activity in the in vivo tests.

It will be apparent to those skilled in the art that numerous changes and modifications can be made in the preferred embodiments of the invention described above without departing from the scope of the invention. Accordingly the foregoing instruction is to be construed in an illustrative and not in a limitative sense, the scope of the invention being defined solely by the appended claims.

We claim:

1. A compound of the formula

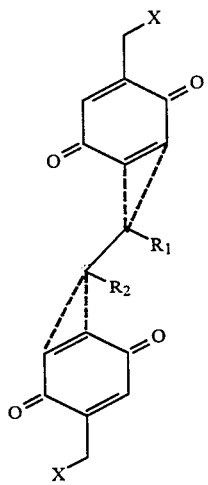

wherein $R_1$ and $R_2$ are each a hydrogen atom or $R_1$ and $R_2$ together form a methylene group, each X is a bromo, iodo or tosyloxy group and the dotted bonds indicate that the central $-CHR_1-CHR_2-$ linkage is attached to the two phenyl rings at positions which are either meta to both $CH_2X$ groups or para to both $CH_2X$ groups.

2. A compound according to claim 1 wherein $R_1$ and $R_2$ together form a methylene group and the central cyclopropylene linkage is para to both $CH_2X$ groups.

3. A compound according to claim 1 wherein $R_1$ and $R_2$ are each a hydrogen atom and the central ethylene linkage is meta to both $CH_2X$ groups.

4. A compound according to claim 1 wherein each X is a bromine atom.

5. A compound according to claim 2 wherein each X is a bromine atom.

6. The compound according to claim 3 wherein each X is a bromine atom, namely 2,2'-ethylenebis[6-(bromomethyl)-p-benzoquinone].

* * * * *